United States Patent [19]

Hara

[11] Patent Number: 5,557,687
[45] Date of Patent: Sep. 17, 1996

[54] ABNORMAL PATTERN DETECTING APPARATUS

[75] Inventor: Shoji Hara, Kanagawa-ken, Japan

[73] Assignee: Fuji Photo Film Co., Ltd., Kanagawa-ken, Japan

[21] Appl. No.: 389,744

[22] Filed: Feb. 15, 1995

Related U.S. Application Data

[63] Continuation of Ser. No. 26,099, Mar. 4, 1993, abandoned, which is a continuation of Ser. No. 599,933, Oct. 19, 1990, abandoned.

[30] Foreign Application Priority Data

Oct. 19, 1989 [JP] Japan ................................. 1-272212

[51] Int. Cl.⁶ ............................................. G06K 9/00
[52] U.S. Cl. .................................... 382/132; 382/283
[58] Field of Search ................................. 382/128, 130, 382/131, 132, 282, 283; 364/413.13, 414.22, 413.16, 414.26; 348/77; 358/453

[56] References Cited

U.S. PATENT DOCUMENTS

| | | | |
|---|---|---|---|
| 3,848,130 | 11/1974 | Macouski | 250/369 |
| 4,258,264 | 3/1981 | Kotera et al. | |
| 4,276,473 | 6/1981 | Kato et al. | |
| 4,315,318 | 2/1982 | Kato et al. | |
| 4,387,428 | 6/1983 | Ishida et al. | |
| 4,710,875 | 12/1987 | Nakajima et al. | |
| 4,769,850 | 9/1988 | Itoh et al. | |
| 4,792,900 | 12/1988 | Sones et al. | 382/6 |
| 4,816,681 | 3/1989 | Shimura | |
| 4,855,598 | 8/1989 | Ohgoda et al. | |
| 4,896,037 | 1/1990 | Shimura et al. | |
| 4,907,156 | 3/1990 | Doi et al. | 382/6 |
| 5,123,054 | 6/1992 | Hara et al. | 382/6 |

FOREIGN PATENT DOCUMENTS

| | | |
|---|---|---|
| 5611395 | 2/1981 | Japan. |
| 615193 | 2/1986 | Japan. |

OTHER PUBLICATIONS

"Detection of Chest X-ray Image Pattern Using Energy Subtraction Image" (by K. Mizutani, J. Hasegawa, J. Toriwaki and H. Nishiya, Denki Kankei Gakkai, Tokai Branch Joint Meeting, 1987, p. 564.

"Automatic Threshold Value Selecting Process Based On Discrimination and Least Square Standards" (by N. Otsu, collected papers of the Institute of Electronics and Communication Engineers of Japan, 63-D-4, pp. 349-356, 19800.

"Discrimination of Rib Patterns in X-ray Fluorographic Image of the Chest" (The Institute of Electronics and Communication Engineers of Japan, Oct. 26, 1972, material No. IT72-24 (1972-10) of the society for the study of image engineering.

*Primary Examiner*—Joseph Mancuso
*Attorney, Agent, or Firm*—Sughrue, Mion, Zinn, Macpeak & Seas

[57] ABSTRACT

An abnormal pattern detecting apparatus comprises an image operating device which generates at least an original image signal representing an original image and a soft tissue image signal representing a soft tissue image from several image signals representing radiation images of an object, which radiation images have been recorded by exposing the object to at least two kinds of radiation having different energy distributions. A region discriminating device discriminates anatomical regions in the radiation image from at least one of the image signals. An abnormal pattern finding device finds an abnormal pattern, which appears in the original image or the soft tissue image, by processing the original image signal or the soft tissue image signal with an abnormal pattern finding filter in accordance with the anatomical regions.

10 Claims, 8 Drawing Sheets

ABNORMAL PATTERN DETECTING APPARATUS

This is a continuation of application Ser. No. 08/026,099 filed Mar. 4, 1993, which is a continuation of application Ser. No. 07/599,933 filed Oct. 19, 1990 both now abandoned.

BACKGROUND OF THE INVENTION

1. Field of the Invention

This invention relates to an abnormal pattern detecting apparatus wherein an abnormal pattern in a radiation image of an object is detected from an image signal made up of a series of image signal components representing the radiation image.

2. Description of the Prior Art

Techniques for reading out a recorded radiation image in order to obtain an image signal, carrying out appropriate image processing on the image signal, and then reproducing a visible image by use of the processed image signal have heretofore been known in various fields. For example, as disclosed in Japanese Patent Publication No. 61(1986)-5193, an X-ray image is recorded on an X-ray film having a small gamma value chosen according to the type of image processing to be carried out, the X-ray image is read out from the X-ray film and converted into an electric signal (image signal), and the image signal is processed and then used for reproducing the X-ray image as a visible image on a copy photograph or the like. In this manner, a visible image having good image quality with high contrast, high sharpness, high graininess, or the like can be reproduced.

Also, when certain kinds of phosphors are exposed to radiation such as X-rays, $\alpha$-rays, $\beta$-rays, $\gamma$-rays, cathode rays or ultraviolet rays, they store part of the energy of the radiation. Then, when the phosphor which has been exposed to the radiation is exposed to stimulating rays such as visible light, light is emitted by the phosphor in proportion to the amount of energy stored thereon during its exposure to the radiation. A phosphor exhibiting such properties is referred to as a stimulable phosphor. As disclosed in U.S. Pat. Nos. 4,258,264, 4,276,473, 4,315,318, 4,387,428, and Japanese Unexamined Patent Publication No. 56(1981)-11395, it has been proposed to use stimulable phosphors in radiation image recording and reproducing systems. Specifically, a sheet provided with a layer of the stimulable phosphor (hereinafter referred to as a stimulable phosphor sheet) is first exposed to radiation which has passed through an object such as the human body in order to store a radiation image of the object thereon, and is then scanned with stimulating rays, such as a laser beam, which cause it to emit light in proportion to the amount of energy stored during exposure to the radiation. The light emitted by the stimulable phosphor sheet, upon stimulation thereof, is photoelectrically detected and converted into an electric image signal. The image signal is then used to reproduce the radiation image of the object as a visible image on a recording material such as photographic film, on a display device such as a cathode ray tube (CRT), or the like.

Radiation image recording and reproducing systems which use stimulable phosphor sheets are advantageous over conventional radiography using silver halide photographic materials, in that images can be recorded even when the energy intensity of the radiation to which the stimulable phosphor sheet is exposed varies over a wide range. More specifically, since the amount of light which the stimulable phosphor sheet emits when being stimulated varies over a wide range and is proportional to the amount of energy stored thereon during its exposure to the radiation, it is possible to obtain an image having a desirable density regardless of the energy intensity of the radiation to which the stimulable phosphor sheet was exposed. In order to obtain the desired image density, an appropriate read-out gain is set when the emitted light is being detected and converted into an electric signal to be used in the reproduction of a visible image on a recording material, such as photographic film, or on a display device, such as a CRT.

Recently, in the radiation image recording and reproducing systems which use X-ray film or stimulable phosphor sheets, particularly in such radiation image recording and reproducing systems designed to facilitate medical diagnosis, not only have image signals been processed in ways which ensure that the visible images produced from them will be of high quality, but image signals have also been processed in ways which allow certain image patterns to be extracted from radiation images. One type of processing which results in extraction of an image pattern is disclosed in, for example, U.S. Pat. No. 4,769,850.

Specifically, an image pattern can be detected in a complicated radiation image by processing the image signal representing it in various ways. The image signal is made up of a series of image signal components, and with appropriate processing the image signal components corresponding to a particular image pattern can be found. For example, from a very complicated radiation image, such as an X-ray image of the chest of a human body, which includes various linear and circular patterns, a pattern corresponding to a tumor, or the like, can be detected.

After a pattern, for example, a tumor pattern, is detected in a complicated radiation image, such as an X-ray image of the chest of a human body, a visible image is reproduced and displayed such that the detected pattern can be viewed clearly. Such a visible image can serve as an effective tool in, particularly, the efficient and accurate diagnosis of an illness.

By way of example, an X-ray image of the chest of a human body, which has been recorded during an ordinary image recording operation, includes both the patterns of soft tissues, such as the heart, the diaphragm, and the lung fields, and the patterns of bones, e.g. the ribs. In cases where operations for automatically finding an abnormal pattern, e.g. a tumor pattern, are carried out on such an ordinary X-ray image of the chest, it may occur that an image pattern, which is not a tumor pattern, is found as a tumor pattern by mistake due to adverse effects of bone patterns. In order that such an error may be avoided, an attempt has been made to obtain an image of only the soft tissues from energy subtraction processing and to find a tumor pattern from the image. Such a technique is described, for example, in "Detection of Chest X-ray Image Pattern Using Energy Subtraction Image" by Katsumi Mizutani, Jun Hasegawa, Junichiro Toriwaki, and Hiroshi Nishiya, Denki Kankei Gakkai, Tokai Branch Joint Meeting, 1987, page 564.

In energy subtraction processing, such characteristics are utilized that a specific structure of an object exhibits different levels of radiation absorptivity with respect to radiation with different energy levels. Specifically, an object is exposed to several kinds of radiation with different energy levels, and a plurality of radiation images are thereby obtained in which different images of a specific structure are embedded. Thereafter, the image signals representing the plurality of the radiation images are weighted appropriately and subjected to a subtraction process in order to extract the image of the specific structure. The applicant proposed novel energy subtraction processing methods using stimulable phosphor sheets in, for example, U.S. Pat. Nos. 4,855,598 and 4,896,037.

In cases where operations for automatically finding an abnormal pattern, e.g. a tumor pattern, are carried out on a radiation image primarily composed of patterns of soft tissues of an object (hereinafter referred to as the "soft tissue image"), instead of a radiation image composed of both the patterns of soft tissues and the patterns of bones of the object (hereinafter referred to as the "original image"), errors in finding an abnormal pattern, which are caused to occur by adverse effects of the bone patterns, can be reduced. However, the soft tissue image is obtained by processing a plurality of radiation images, and therefore the image quality of the soft tissue image is worse than the original image. Therefore, the problems occur in that errors in finding an abnormal pattern increase due to bad image quality of the soft tissue image.

SUMMARY OF THE INVENTION

The primary object of the present invention is to provide an abnormal pattern detecting apparatus wherein the accuracy, with which an abnormal pattern is detected automatically, is kept high.

FIG. 1 is a block diagram showing the configuration of an abnormal pattern detecting apparatus in accordance with the present invention.

With reference to FIG. 1, a plurality of image signals SO1, SO2, ..., SOn are fed from, for example, a radiation image read-out apparatus or a radiation image signal storage device, into an image operating means 1. The plurality of the image signals SO1, SO2, ..., SOn represent radiation images of an object, which were recorded during an image recording operation wherein the object constituted of soft tissues and bones was exposed to at least two kinds of radiation having different energy distributions. The image operating means 1 carries out operations on the plurality of the image signals SO1, SO2, ..., SOn in order to generate an original image signal S1, which represents an original image composed of both the patterns of soft tissues and the patterns of bones of the object, and a soft tissue image signal S2, which represents a soft tissue image primarily composed of the patterns of soft tissues of the object. In the image operating means 1, a bone image signal S3 may also be generated which represents a bone image primarily composed of the patterns of bones of the object.

The original image signal S1 and the soft tissue image signal S2 generated by the image operating means 1 are fed from the image operating means 1 into an abnormal pattern finding means 3. In cases where the bone image signal S3 is also generated by the image operating means 1, it is fed into the abnormal pattern finding means 3 (or into a region discriminating means 2 which will be described later).

Also, an image signal, from which information about anatomical regions in the radiation image of the object can be found, is fed from the image operating means 1 into the region discriminating means 2. By way of example, as such an image signal, one of the image signals SO1, SO2, ..., SOn, or an original image signal S1, which has been obtained from the processing carried out on the image signals SO1, SO2, ..., SOn, may be employed.

From the received image signal, the region discriminating means 2 discriminates anatomical regions D1, D2, ..., Dn in the radiation image of the object from one another, and generates information about the positions of the anatomical regions D1, D2, ..., Dn.

The term "anatomical regions" as used herein means the regions corresponding to the patterns of the structures of the object, which patterns appear in the radiation image. Specifically, the term "anatomical regions" as used herein means the regions corresponding to the patterns of the lung fields, a rib, the heart, the diaphragm, and the like, in an X-ray image of the chest. Of course, the region discriminating means 2 need not necessarily discriminate all of the regions corresponding to the patterns of the structures of the object from one another, which patterns appear in the radiation image, but may find only the necessary anatomical regions in accordance with the type of the abnormal patterns which are to be found. For example, in cases where an abnormal pattern in the lung region is to be detected, the region discriminating means 2 may discriminate only two regions, i.e. a region corresponding to the diaphragm and the heart and the other region, from each other.

The information about the positions of the anatomical regions D1, D2, ..., Dn, which have been found by the region discriminating means 2, is fed into the abnormal pattern finding means 3.

The abnormal pattern finding means 3 processes the original image signal S1 or the soft tissue image signal S2 with an abnormal pattern finding filter in accordance with the anatomical regions D1, D2, ..., Dn, which have been discriminated by the region discriminating means 2. In this manner, the abnormal pattern finding means 3 finds an abnormal pattern which appears in the original image or the soft tissue image. No limitation is imposed on the abnormal pattern finding filter. By way of example, one of various filters which will be described later, or a combination of two or more of the filters may be employed. Alternatively, any of known filters may be employed. By way of example, the abnormal pattern finding filter used to process the original image signal S1 may be selected from those which are suitable for finding an abnormal pattern in the original image. Also, the abnormal pattern finding filter used to process the soft tissue image signal S2 may be selected from those which are suitable for finding an abnormal pattern in the soft tissue image. In this manner, different filters may be employed during the processing of the original image signal S1 and during the processing of the soft tissue image signal S2. Additionally, in cases where the image signal components corresponding to a plurality of anatomical regions in the original image are to be processed, different filters may be employed for the image signal components corresponding to different anatomical regions. In this manner, different filters may be employed for different anatomical regions in the original image or the soft tissue image. (Such a technique is proposed in U.S. patent application Ser. No. 543,530.)

The term "abnormal pattern" as used herein means a pattern, which does not occur in standard patterns, for example, a pattern corresponding to a tumor, a calcified part, a fattened and thickened pleura, or a pneumothorax in an X-ray image of the chest. The abnormal pattern finding means 3 need not necessarily find all types of abnormal patterns, but may find only the patterns of, for example, tumors as the abnormal patterns.

As described above, the bone image signal S3 may also be fed into the abnormal pattern finding means 3. The bone image signal S3 may be utilized such that the mode of the processing with an abnormal pattern finding filter may be changed over between the processing of the original image signal S1 and the processing of the soft tissue image signal S2. By way of example, in cases where an anatomical region found by the region discriminating means 2 (e.g. the region corresponding to the lung field in an X-ray image of the chest) is composed of soft tissue patterns and bone patterns, the anatomical region may be divided into a region composed of the soft tissue patterns and a region composed of the bone patterns. When the image signal components corresponding to the region composed of the soft tissue patterns are processed with an abnormal pattern finding filter, the processing may be carried out on the corresponding region in the original image, which has better image quality than the soft tissue image. When the image signal components corresponding to the region composed of the bone patterns are processed with an abnormal pattern finding filter, the processing may be carried out on the corresponding region in the soft tissue image so that the detection of an abnormal pattern may not be adversely affected by the bone patterns.

Also, as described above, the bone image signal S3 may also be fed into the region discriminating means 2. Alternatively, the bone image signal S3 may be generated by the region discriminating means 2. When an anatomical region composed of soft tissue patterns and bone patterns is found, the region discriminating means 2 may utilize the bone image signal S3 in order to discriminate that the soft tissue patterns and the bone patterns constitute different anatomical regions.

Instead of the original image signal S1 and the soft tissue image signal S2 being processed independently in accordance with the anatomical regions, a new image signal representing a new image may be generated by combining the original image signal S1 and the soft tissue image signal S2 in the manner disclosed in, for example, U.S. Pat. No. 4,816,681. The new image signal thus generated may then be processed with an abnormal pattern finding filter. The term "processing an original image signal or a soft tissue image signal in accordance with anatomical regions" as used herein also embraces such cases.

With the abnormal pattern detecting apparatus in accordance with the present invention, at least the original image signal S1, which represents the original image, and the soft tissue image signal S2, which represents the soft tissue image, are generated from the plurality of the image signals SO1, SO2, . . . , SOn representing a plurality of radiation images of an object which were recorded with radiation having different energy distributions. Also, the anatomical regions in the radiation image are found. The original image signal or the soft tissue image signal is processed with an abnormal pattern finding filter in accordance with the anatomical regions, and an abnormal pattern is thereby found. Therefore, an abnormal pattern can be detected more accurately than with a conventional abnormal pattern detecting apparatus wherein an abnormal pattern is detected from the original image or from the soft tissue image.

DESCRIPTION OF THE PREFERRED EMBODIMENTS

The present invention will hereinbelow be described in further detail with reference to the accompanying drawings.

In an embodiment described hereinbelow, X-ray images are stored on stimulable phosphor sheets, and a pattern of a tumor, which typically has an approximately spherical shape in the lungs of a human body, is detected as an abnormal pattern from the X-ray images. In a visible image reproduced from an image signal representing the X-ray image, the tumor pattern typically appears as an approximately circular pattern having a lower density than the areas of the image surrounding the tumor pattern.

Figure 2:
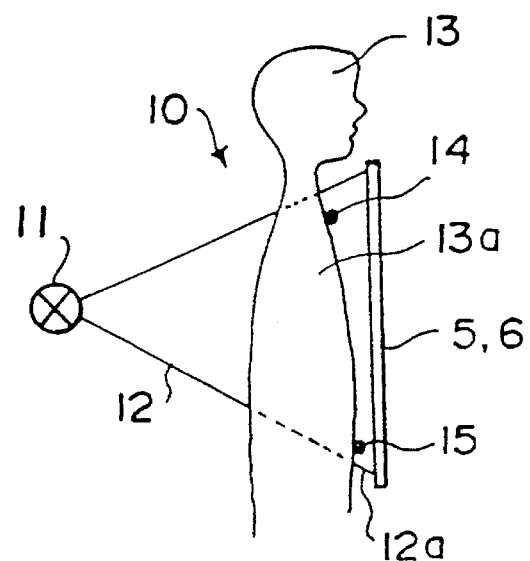
FIG. 2 is a schematic view showing an example of an X-ray image recording apparatus.

FIG. 2 is a schematic view showing an example of an X-ray image recording apparatus.

With reference to FIG. 2, X-rays 12 are produced by an X-ray source 11 of an X-ray image recording apparatus 10 and irradiated to the chest 13a of a human body 13. X-rays 12a, which have passed through the human body 13, impinge upon a first stimulable phosphor sheet 5. In this manner, a first X-ray image of the chest 13a of the human body 13 is stored on the first stimulable phosphor sheet 5.

Thereafter, the first stimulable phosphor sheet 5 is quickly removed from the X-ray image recording apparatus 10, and a second stimulable phosphor sheet 6 is quickly set therein. Also, the tube voltage of the X-ray source 11 is changed. The X-ray image recording operation is then carried out for the second stimulable phosphor sheet 6. In this manner, a second X-ray image of the same object 13 is stored on the second stimulable phosphor sheet 6 with X-rays, which have a different energy distribution than the X-rays used during the recording of the first X-ray image on the first stimulable phosphor sheet 5. The object 13 is provided with marks 14 and 15, and images of the marks 14 and 15 are also recorded on the first stimulable phosphor sheet 5 and the second stimulable phosphor sheet 6. As an aid in facilitating the explanation, the reference numerals 14 and 15 will hereinafter denote both the marks and the images thereof. The marks 14 and 15 are used when the positions of the first X-ray image stored on the first stimulable phosphor sheet 5 and the second X-ray image stored on the second stimulable phosphor sheet 6 are adjusted so that they coincide with each other.

Figure 3:
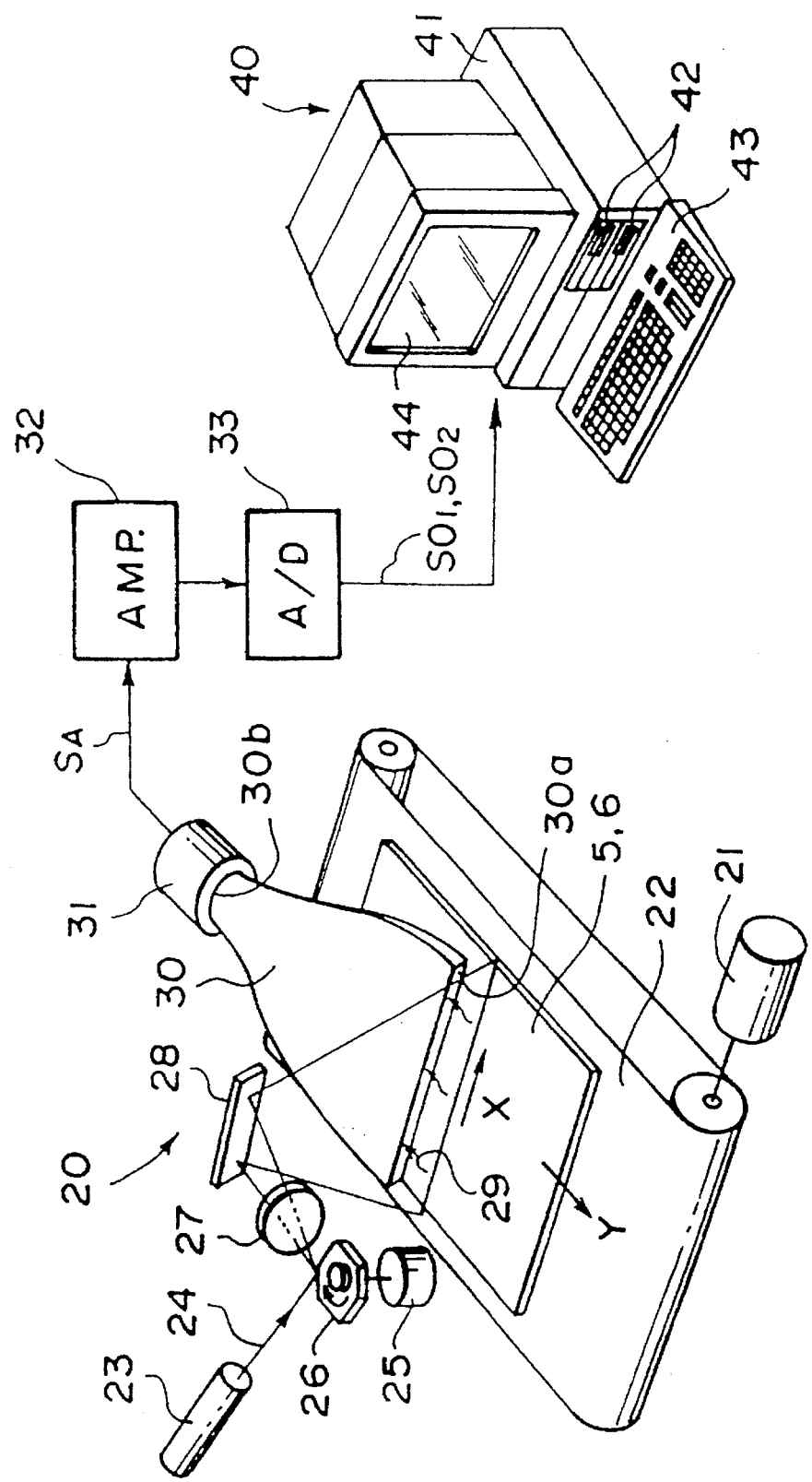
FIG. 3 is a perspective view showing an example of an X-ray image read-out apparatus and a computer system which is provided with an embodiment of the abnormal pattern detecting apparatus in accordance with the present invention.

FIG. 3 is a perspective view showing an example of an X-ray image read-out apparatus and a computer system which is provided with an embodiment of the abnormal pattern detecting apparatus in accordance with the present invention.

After the image recording operations are carried out with the X-ray image recording apparatus 10 shown in FIG. 2, the first stimulable phosphor sheet 5 and the second stimulable phosphor sheet 6 are set one after another at a predetermined position in an X-ray image read-out apparatus 20 shown in FIG. 3. How the first X-ray image is read out from the first stimulable phosphor sheet 5 will be described hereinbelow.

The first stimulable phosphor sheet 5, on which the first X-ray image has been stored and which has been placed at the predetermined position in the X-ray image read-out apparatus 20, is conveyed in a sub-scanning direction indicated by the arrow Y by a sheet conveyance means 22, which is constituted of an endless belt or the like and which is operated by a motor 21. A laser beam 24, which serves as stimulating rays, is produced by a laser beam source 23, and is reflected and deflected by a rotating polygon mirror 26 which is quickly rotated by a motor 25 in the direction indicated by the arrow. The laser beam 24 then passes through a converging lens 27 constituted of an fθ lens or the like. The direction of the optical path of the laser beam 24 is then changed by a mirror 28, and the laser beam 24 impinges upon the stimulable phosphor sheet 5 and scans it in a main scanning direction indicated by the arrow X, which direction is approximately normal to the sub-scanning direction indicated by the arrow Y. When the stimulable phosphor sheet 5 is exposed to the laser beam 24, the exposed portion of the stimulable phosphor sheet 5 emits light 29 in an amount proportional to the amount of energy stored thereon during its exposure to the X-rays. The emitted light 29 is guided by a light guide member 30 and photoelectrically detected by a photomultiplier 31. The light guide member 30 is made from a light guiding material such as an acrylic plate and has a linear light input face 30a, positioned so that it extends along the main scanning line on the stimulable phosphor sheet 5, and a ring-shaped light output face 30b, positioned so that it is in close contact with a light receiving face of the photomultiplier 31. The emitted light 29, which has entered the light guide member 30 at its light input face 30a, is guided through repeated total reflection inside of the light guide member 30, emanates from the light output face 30b, and is received by the photomultiplier 31. In this manner, the amount of the emitted light 29, which amount represents the X-ray image, is converted into an electric signal by the photomultiplier 31.

An analog output signal SA generated by the photomultiplier 31 is logarithmically amplified by a logarithmic amplifier 32, and digitized by an A/D converter 33 into an electric image signal SO.

The image signal SO is then fed into a computer system 40. The image signal SO thus obtained represents the first X-ray image, which was stored on the first stimulable phosphor sheet 5. Therefore, the image signal SO thus obtained will hereinbelow be referred to as the first image signal SO1.

The computer system 40 is provided with an embodiment of the abnormal pattern detecting apparatus in accordance with the present invention. The computer system 40 comprises a main body 41 in which a CPU and an internal memory are incorporated, a disk drive unit 42 which operates a floppy disk serving as a subsidiary memory, a keyboard 43 from which necessary instructions, or the like, are fed into the computer system 40, and a CRT display device 44 which displays necessary information.

Thereafter, in the same manner as that described above, a second image signal SO2 is obtained, which represents the second X-ray image stored on the second stimulable phosphor sheet 6. The second image signal SO2 is fed into the computer system 40.

From the first image signal SO1 and the second image signal SO2 which have been fed into the computer system 40, an abnormal pattern in the X-ray image is detected. The computer system 40 carries out the operations corresponding to the blocks 1, 2, and 3 shown in FIG. 1. The blocks 1, 2, and 3 shown in FIG. 1 will hereinafter be referred to as the blocks representing the functions of the computer system 40.

Figure 1:
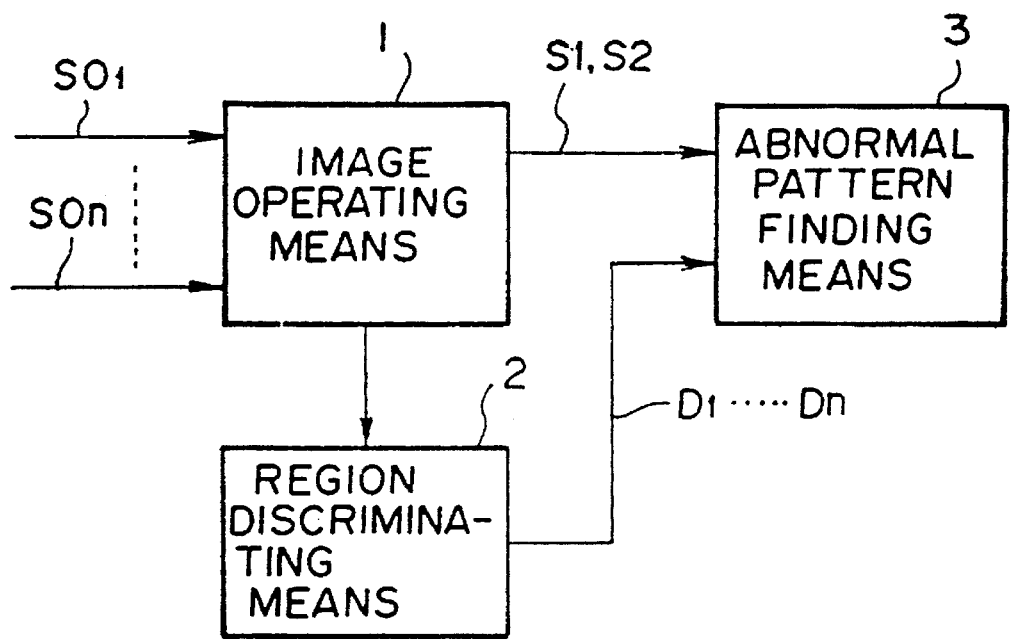
FIG. 1 is a block diagram showing the abnormal pattern detecting apparatus in accordance with the present invention.

The image signals SO1 and SO2, which are digital electric signals representing the first and second X-ray images, are fed into the image operating means 1 of the computer system 40, which image operating means 1 is shown in FIG. 1.

Image Operating Means

As described above, the first image signal SO1 and the second image signal SO2 represent the first and second X-ray images, which were recorded with the X-rays having different energy distributions. The X-rays having different energy distributions exhibit different transmittances with respect to soft tissues and bones of the object (the chest of a human body in this case). Therefore, by carrying out the subtraction processing on the first and second X-ray images, an image of only the soft tissues of the object (i.e. a soft tissue image) and an image of only the bones of the object (i.e. a bone image) can be obtained.

From the first image signal SO1 and the second image signal SO2, the image operating means 1 of the computer system 40 adjusts the positions of the first and second X-ray images in the manner described below. In this embodiment, the process for adjusting the positions is employed which is disclosed in U.S. Pat. No. 4,710,875.

The marks 14 and 15 in the first X-ray image represented by the first image signal SO1 will hereinbelow be referred to as the marks 14' and 15'. Also, the marks 14 and 15 in the second X-ray image represented by the second image signal SO2 will hereinbelow be referred to as the marks 14" and 15". The marks 14' and 15' respectively have coordinates (XA1,YA1) and coordinates (XA2,YA2). The marks 14" and 15" respectively have coordinates (XB1,YB1) and coordinates (XB2,YB2).

The following formula obtains:

$$\theta = \tan^{-1}\left(\frac{Y_{B2} - Y_{B1}}{X_{B2} - X_{B1}}\right) - \tan^{-1}\left(\frac{Y_{A2} - Y_{A1}}{X_{A2} - X_{A1}}\right) \quad (1)$$

where θ denotes the angle of rotation between the two X-ray images, i.e. the angle between the line, which connects the coordinates (XA1,YA1) and the coordinates (XA2,YA2), and the line, which connects the coordinates (XB1,YB1) and the coordinates (XB2,YB2). The positions of the two X-ray images can be caused to coincide with each other by rotating the first X-ray image by the angle θ.

A shift ΔX1 along the x direction between the marks 14' and 14" in the two X-ray images and a shift ΔY1 along the y direction between the marks 14' and 14" in the two X-ray images are expressed as $$\Delta X_1 = X_{B1} - \{\alpha \cdot (X_{A1} - C_X) \cdot \cos\theta - \alpha(Y_{A1} - C_Y) \cdot \sin\theta + C_X\} \quad (2)$$

$$\Delta Y_1 = Y_{B1} - \{\alpha \cdot (X_{A1} - C_X) \cdot \sin\theta + \alpha(Y_{A1} - C_Y) \cdot \cos\theta + C_Y\} \quad (3)$$

Also, a shift ΔX2 along the x direction between the marks 15' and 15" in the two X-ray images and a shift ΔY2 along the y direction between the marks 15' and 15" in the two X-ray images are expressed as $$\Delta X_2 = X_{B2} - \{\alpha \cdot (X_{A2} - C_X) \cdot \cos\theta - \alpha(Y_{A2} - C_Y) \cdot \sin\theta + C_X\} \quad (4)$$

$$\Delta Y_2 = Y_{B2} - \{\alpha \cdot (X_{A2} - C_X) \cdot \sin\theta + \alpha(Y_{A2} - C_Y) \cdot \cos\theta + C_Y\} \quad (5)$$

In Formulas (2) through (5), CX and CY respectively denote the X and Y coordinates of the center of rotation.

In ideal cases, ΔX1 and ΔX2 will be equal to each other. Also, ΔY1 and ΔY2 will be equal to each other. However, in some cases, they will not be equal to each other because of errors in sampling of the image signals SO1 and SO2. Therefore, position adjustment amounts ΔX and ΔY along the X and Y directions are calculated from the formulas $$\Delta X = (\Delta X_1 + \Delta X_2)/2 \quad (6)$$

$$\Delta Y = (\Delta Y_1 + \Delta Y_2)/2 \quad (7)$$

The amounts thus calculated are used during the adjustment of the position of the first X-ray image along the X and Y directions.

In the manner described above, a first image signal SO1' and a second image signal SO2' are obtained, which respectively represent the first and second X-ray images whose positions have been adjusted. Thereafter, in the image operating means 1, superposition processing is carried out on the first image signal SO1' and the second image signal SO2'. Specifically, the image signal components of the first image signal SO1' and the second image signal SO2' which represent corresponding picture elements in the two X-ray images are added together. The superposition processing is expressed as $$S1 = Wa \cdot SO_1' + Wb \cdot SO_2' \quad (8)$$

where Wa and Wb denote weighting coefficients. In this manner, an original image signal S1 representing an original image, which is composed of both the soft tissue patterns and the bone patterns, is obtained from the superposition processing. Either one of the first and second X-ray images may be employed as the original image. However, in this embodiment, in order that noise occurring in the X-ray image due to, for example, sway of the X-rays during the image recording operation may be reduced, superposition processing is carried out with Formula (8), and the image obtained from the superposition processing is employed as the original image.

Also, a soft tissue image signal S2 representing a soft tissue image is generated by carrying out subtraction processing on the first image signal SO1' and the second signal SO2' which respectively represent the first and second X-ray images whose positions have been adjusted. Specifically, the image signal components of the first image signal SO1' and the second image signal SO2' which represent corresponding picture elements in the two X-ray images are subtracted from each other. The subtraction processing is expressed as $$S2 = Wa' \cdot SO_1' - Wb' \cdot SO_2' + C' \quad (9)$$

where Wa' and Wb' denote weighting coefficients, and C' denotes the bias component.

In this embodiment, a bone image signal S3 representing a bone image may optionally be generated. For this purpose, the weighting coefficients and the bias component are changed from those in Formula (9), and the image signal components of the first image signal SO1' and the second image signal SO2' which represent corresponding picture elements in the two X-ray images are subtracted from each other. The subtraction processing is expressed as $$S3 = Wa'' \cdot SO_1' - Wb'' \cdot SO_2' + C'' \quad (10)$$

where Wa" and Wb" denote weighting coefficients, and C" denotes the bias component.

In this embodiment, the image operating means 1 finds the original image, the soft tissue image, and the bone image from the image signals SO1 and SO2 representing the two X-ray images. Alternatively, the image operating means 1 may find the original image, the soft tissue image, and the bone image from a plurality of the image signals SO1, SO2, . . . , SOn. (Such a technique is disclosed in U.S. Pat. No. 4,855,598.)

Figure 4A:
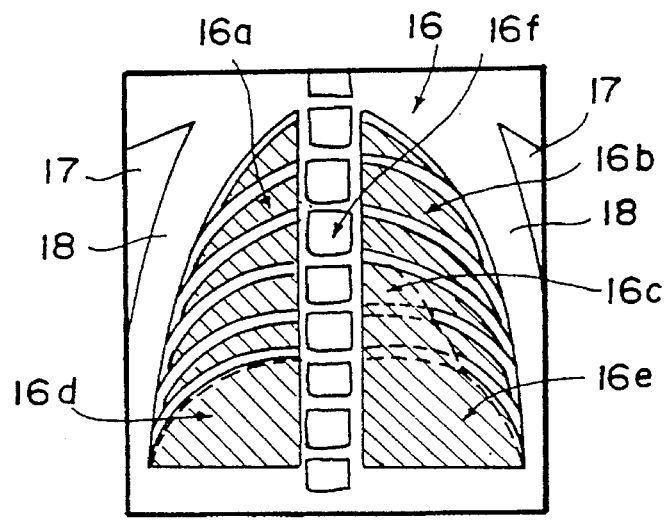
FIGS. 4A, 4B, and 4C are schematic view showing examples of an original image, a soft tissue image, and a bone image.
Figure 4B:
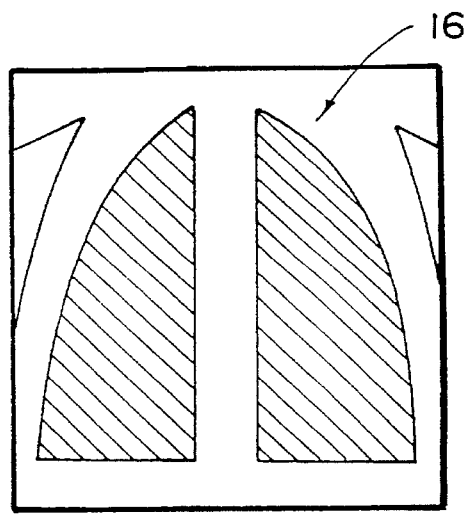
Figure 4C:
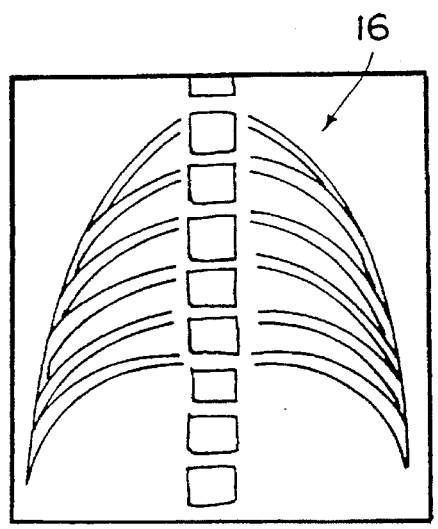

FIGS. 4A, 4B, and 4C show examples of the original image, the soft tissue image, and the bone image.

In the original image shown in FIG. 4A, each of a right lung field region 16a and a left lung field region 16b in a lung region 16 is composed of a soft tissue pattern and bone (rib) patterns. Because the heart (soft tissue) is comparatively thick, a heart region 16c is predominantly composed of a soft tissue pattern. A right diaphragm region 16d and a left diaphragm region 16e are composed of soft tissues. A mediastinum region 16f is composed of bone patterns. In this manner, the original image is composed of both the soft tissue patterns and the bone patterns.

In the soft tissue image shown in FIG. 4B, the bone patterns have been eliminated from the lung region 16, and only the patterns of the soft tissues are formed.

Also, the bone image shown in FIG. 4C is composed of the patterns of the bones, such as the mediastinum and the ribs.

The original image signal S1 and the soft tissue image signal S2 generated by the image operating means 1 of the computer system 40 are fed into the abnormal pattern finding means 3 of the computer system 40.

Also, in this embodiment, anatomical regions are discriminated from one another from the original image signal S1. For this purpose, the original image signal S1 is also fed into the region discriminating means 2 of the computer system 40. Additionally, in this embodiment, the bone image signal S3 is fed into the region discriminating means 2.

When necessary, the image operating means 1 carries out other image processing, such as frequency response enhancement processing, smoothing processing, or noise elimination processing on the first image signal SO1 and the second image signal SO2, or on the original image signal S1, the soft tissue image signal S2, and the bone image signal S3.

Region Discriminating Means

From the original image signal S1, the region discriminating means 2 of the computer system 40 discriminates anatomical regions 16a through 16f in the lung region 16 shown in FIG. 4A.

Figure 5:
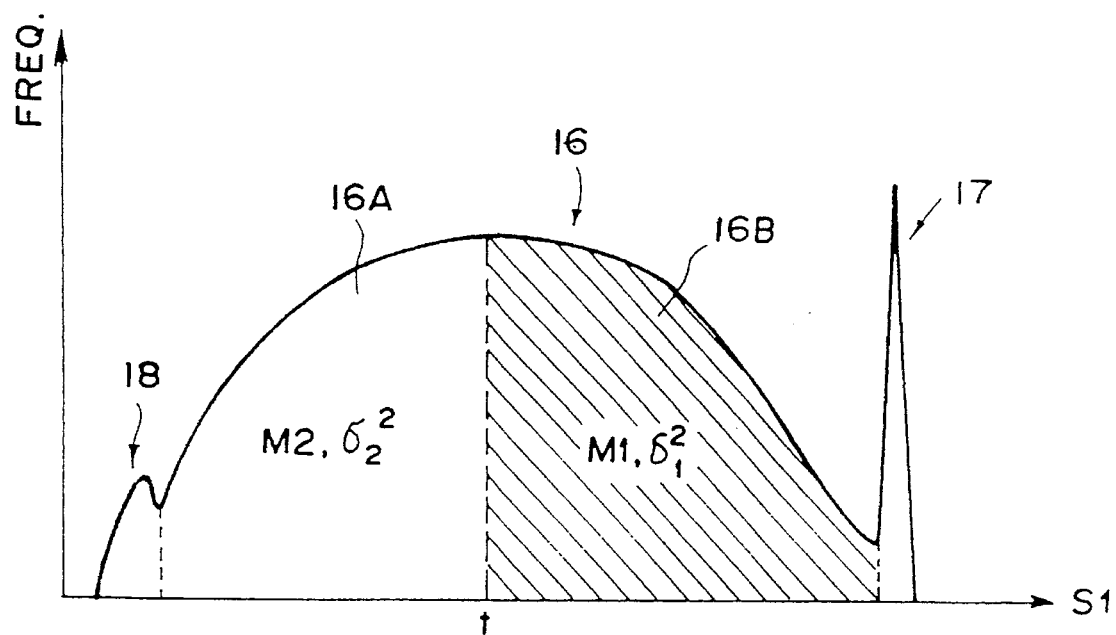
FIG. 5 is a graph showing an example of a probability density function of an image signal.

FIG. 5 is a graph showing an example of a probability density function of the original image signal S1. In FIG. 5, the horizontal axis indicates the value of the original image signal S1, and the vertical axis indicates the frequency of occurrence of the value of the original image signal S1.

Figure 6:
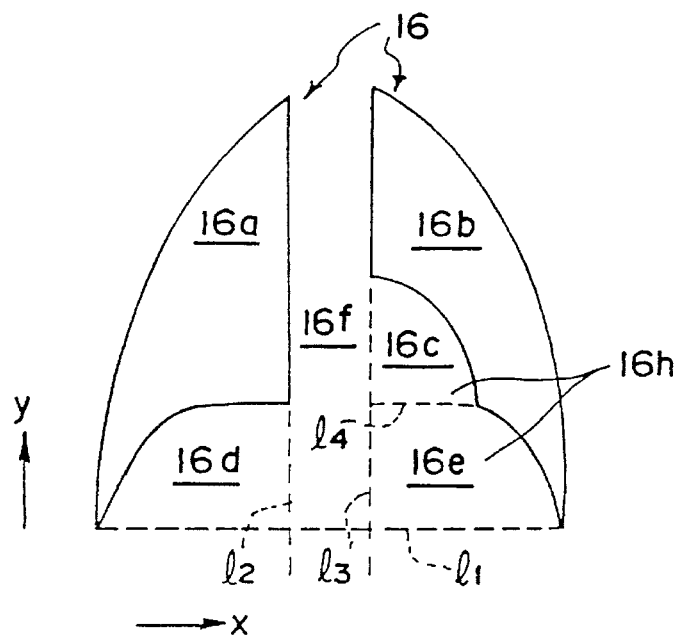
FIG. 6 is an explanatory view showing how the positions of anatomical regions in the X-ray image of the chest are detected.

FIG. 6 is an explanatory view showing how the positions of the regions 16a through 16f in the lung region 16 are detected.

With reference to FIG. 5, a projecting part 17, which is present on the right side, corresponds to a background region 17 shown in FIG. 4A, upon which the X-rays impinged directly without passing through the object 2 shown in FIG. 2 during the image recording operation. A projecting part 16 in the middle corresponds to the lung region 16 shown in FIG. 4A. Also, a projecting part 18 on the left side corresponds to a skin region 18 shown in FIG. 4A. As an aid in facilitating the explanation, in FIG. 5, the projecting parts corresponding to the regions shown in FIG. 4A are numbered with corresponding reference numerals.

In this embodiment, the right lung field region 16a and the left lung field region 16b are first found in the manner described below. The process used for this purpose is described "Automatic Threshold Value Selecting Process Based On Discrimination And Least Square Standards" by Nobuyuki Otsu, collected papers of The Institute of Electronics and Communication Engineers of Japan, 63-D-4, pp. 349–356, 1980.

A threshold value t is determined such that the value calculated with the formula $$\frac{M1 - M2}{\sigma1^2 + \sigma2^2}$$

becomes the largest. In this formula, M1 and $\sigma1^2$ denote respectively the mean value and the variance of the values of the original image signal S1, which values are larger than the threshold value t. Also, M2 and $\sigma2^2$ denote respectively the mean value and the variance of the values of the original image signal S1, which values are smaller than the threshold value t. Thereafter, from the image signal components of the original image signal S1 corresponding to the projecting part 16, the image signal components having values larger than the threshold value t are extracted. Two regions, which are composed of the picture elements corresponding to the thus extracted image signal components and which have comparatively large areas, are found as corresponding to the right lung field region 16a and the left lung field region 16b as shown in FIG. 6.

Thereafter, as shown in FIG. 6, a line 11 is drawn which connects the bottom edges of the right lung field region 16a and the left lung field region 16b. The right edge of right lung field region 16a, which right edge is taken in the X-ray image shown in FIG. 6, is approximated by a straight line, and a line 12 is extended downwardly from the straight line. Also, the upper one-third part of the left edge of the left lung field region 16b, which left edge is taken in the X-ray image shown in FIG. 6, is approximated by a straight line, and a line 13 is extended downwardly from the straight line. In this manner, a region 16h is found which comprises the right diaphragm region 16d, the mediastinum region 16f, the heart region 16c, and the left diaphragm region 16e.

In cases where the heart region 16c and the left diaphragm region 16e are to be discriminated from each other, operations are carried out in the manner described below. Specifically, from the image signal components of the original image signal S1 representing the picture elements, which are considered to be located in the vicinity of the boundary between the heart region 16c and the left diaphragm region 16e in the region 16h, calculations are made to find differences between the values of the image signal components representing the picture elements which are adjacent to each other in the vertical direction, which vertical direction is taken in FIG. 6. The picture elements, for which the differences are larger than a predetermined value, are imaginarily plotted on the X-ray image. A line 14, which connects the thus plotted picture elements and which extends horizontally in FIG. 6, is found to be the boundary between the heart region 16c and the left diaphragm region 16e. In this manner, the positions of the regions 16a through 16f in the X-ray image are detected.

In this embodiment, the region discriminating means 2 also detects the positions of rib patterns (shown in FIG. 4A) in the right lung field region 16a and the left lung field region 16b.

In order for the rib patterns to be found, by way of example, the original image signal S1 may be processed with a method which is described in "Discrimination of Rib Patterns in X-ray Fluorographic Image of the Chest", The Institute of Electronics and Communication Engineers of Japan, Oct. 26, 1972, material No. IT72-24 (1972-10) of the society for the study of image engineering. With the method, a linear figure is extracted by processing an image signal representing an X-ray image of the chest with a filter, which is sensitive to lines. From the position of the linear figure in the X-ray image, the direction along which the linear figure extends, or the like, lines corresponding to a rib pattern are detected. Thereafter, boundary lines of the rib pattern are approximately represented by a function of second order. In this manner, a rib pattern is extracted.

In this embodiment, because the bone image signal S3 representing the bone image has been generated by the image operating means 1, the bone image signal S3 is fed into the region discriminating means 2. In such cases, in the manner described below, the bone patterns can be found more easily than the aforesaid method.

Figure 7A:
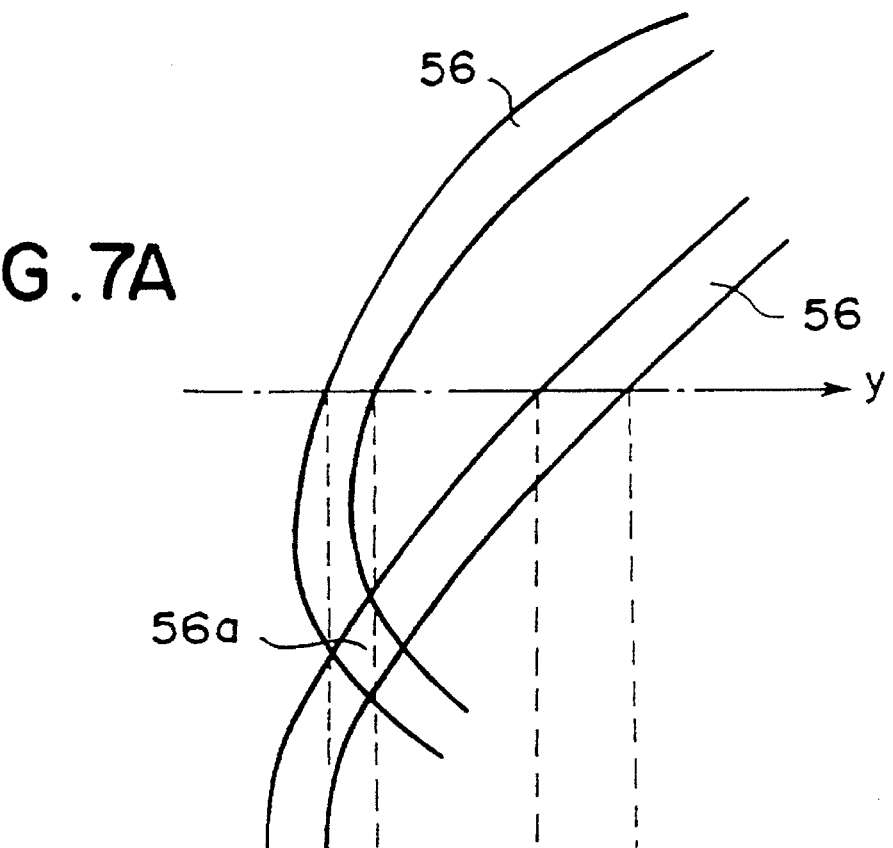
FIG. 7A is an enlarged view showing part of the bone image shown in FIG. 4C.
Figure 7B:
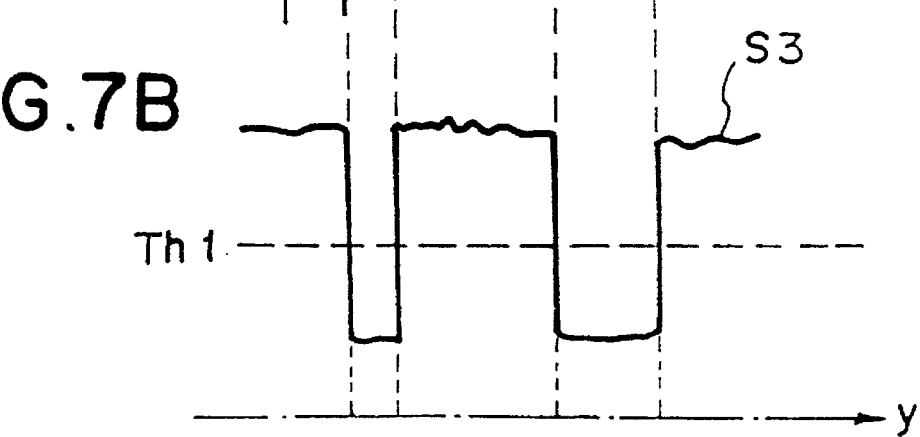
FIG. 7B is a graph showing the bone image signal S3 which corresponds to the part of the bone image shown in FIG. 7A.

As an aid in explaining how the information about the positions of the bone patterns in the bone image is found, FIG. 7A shows part of the bone image shown in FIG. 4C, and FIG. 7B shows the bone image signal S3 which corresponds to the part of the bone image shown in FIG. 7A.

The part of the bone image shown in FIG. 7A includes two rib patterns 56, 56. The two rib patterns 56, 56 overlap one upon the other at part 56a. The graph of FIG. 7B shows the levels of the image signal components of the bone image signal S3 representing the picture elements arrayed along the y axis in FIG. 7A. Because the bone image is composed only of the bone patterns, the regions corresponding to the bone patterns and the other region can be clearly discriminated from each other. Therefore, by investigating whether the levels of the image signal components of the bone image signal S3 are or are not lower than a threshold value Th1, it can be found whether a certain region corresponds or does not correspond to the bone patterns. In this manner, the information about the positions of the bone patterns can be obtained. In cases where the part 56a, at which the rib patterns 56, 56 overlap one upon the other, is to be detected, it can be detected by, for example, approximately representing the rib patterns 56, 56 with curves of secondary order and finding a region at which the approximate curves intersect with each other.

In cases where the information about the positions of the bone patterns is to be found from the bone image signal S3, the method employed for this purpose is not limited to the processing with the threshold value. For example, the information about the positions of the bone patterns may be found by carrying out differentiation processing on the image signal components of the bone image signal S3 and detecting the positions, which correspond to peaks of the values resulting from the differentiation processing.

The information about the positions of the regions 16a through 16f in the lung region 16 and the information about the positions of the rib patterns, or the like, which have been obtained in the manner described above, are fed into the abnormal pattern finding means 3.

No limitation is imposed on how the regions 16a through 16f and rib patterns in the X-ray image are detected.

Abnormal Pattern Finding Means

The abnormal pattern finding means 3, which is provided in the computer system 40, finds tumor patterns, which appear in the original image or the soft tissue image. For this purpose, the abnormal pattern finding means 3 processes the original image signal S1 or the soft tissue image signal S2 with a tumor pattern finding spatial-domain filter in accordance with the information about the anatomical regions (in this embodiment, the information about the regions 16a through 16f in the lung region 16 shown in FIG. 6) and the information about the rib patterns shown in FIG. 4A. The abnormal pattern finding means 3 works in the manner described below.

The diaphragm regions 16d and 16e in the lung region 16 shown in FIG. 6 correspond to the regions in the original image shown in FIG. 4A, which regions are composed of only the soft tissue patterns. Therefore, as for the diaphragm regions 16d and 16e, the processing with the abnormal pattern finding filter is carried out on the corresponding image signal components of the original image signal S1. The heart region 16c corresponds to the region in the original image, which region is predominantly composed of the soft tissue pattern. Therefore, as for the heart region 16c, the processing with the abnormal pattern finding filter is carried out on the corresponding image signal components of the original image signal S1. The lung field regions 16a and 16b are composed of soft tissue patterns and the bone (rib) patterns. Therefore, as for the areas of the lung field regions 16a and 16b other than the rib patterns, the processing with the abnormal pattern finding filter is carried out on the corresponding image signal components of the original image signal S1. Also, as for the areas of the rib patterns in the lung field regions 16a and 16b, the processing with the abnormal pattern finding filter is carried out on the corresponding image signal components of the soft tissue image signal S2. In cases where the information about the positions of the rib patterns is not used, the processing with the abnormal pattern finding filter is carried out on the image signal components of the soft tissue image signal S2, which correspond to the whole area of the lung field regions 16a and 16b. This is because, if the processing with the abnormal pattern finding filter is carried out on the image signal components of the original image signal S1, which correspond to the whole area of the lung field regions 16a and 16b, errors in finding tumor patterns will increase due to the adverse effects of the rib patterns.

Figure 8:
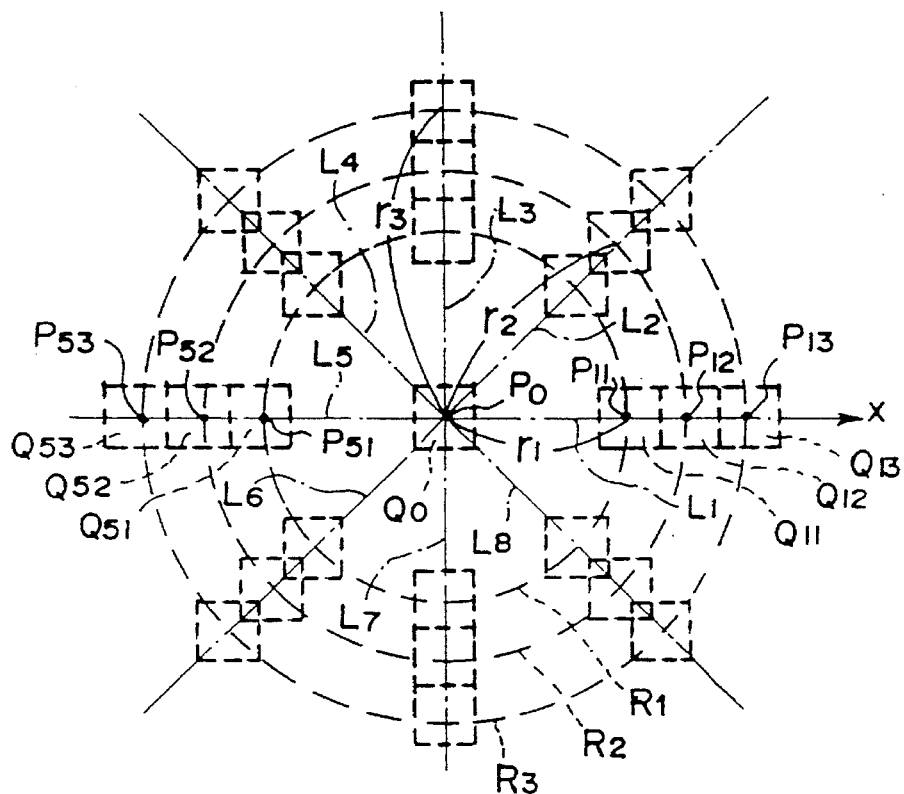
FIG. 8 is a diagram having a predetermined picture element P0 from an X-ray image in the middle, which diagram serves as an aid in explaining how a spatial-domain filter works during the operations for finding a tumor pattern.

FIG. 8 is a diagram having a predetermined picture element P0 from an X-ray image in the middle, which diagram serves as an aid in explaining how a spatial-domain filter works during the operations for finding a tumor pattern. A judgment is made as to whether a predetermined picture element P0 in the X-ray image falls or does not fall within the region corresponding to the tumor pattern in the X-ray image. The tumor pattern, which appears in the original image or the soft tissue image can be detected by processing the image signal components representing the picture elements of the original image or the soft tissue image with the filter illustrated in FIG. 8 in accordance with the anatomical regions. How the original image signal S3 is processed with the filter will mainly be described below. The filter described first is disclosed in U.S. patent application Ser. No. 542,487.

Figure 9:
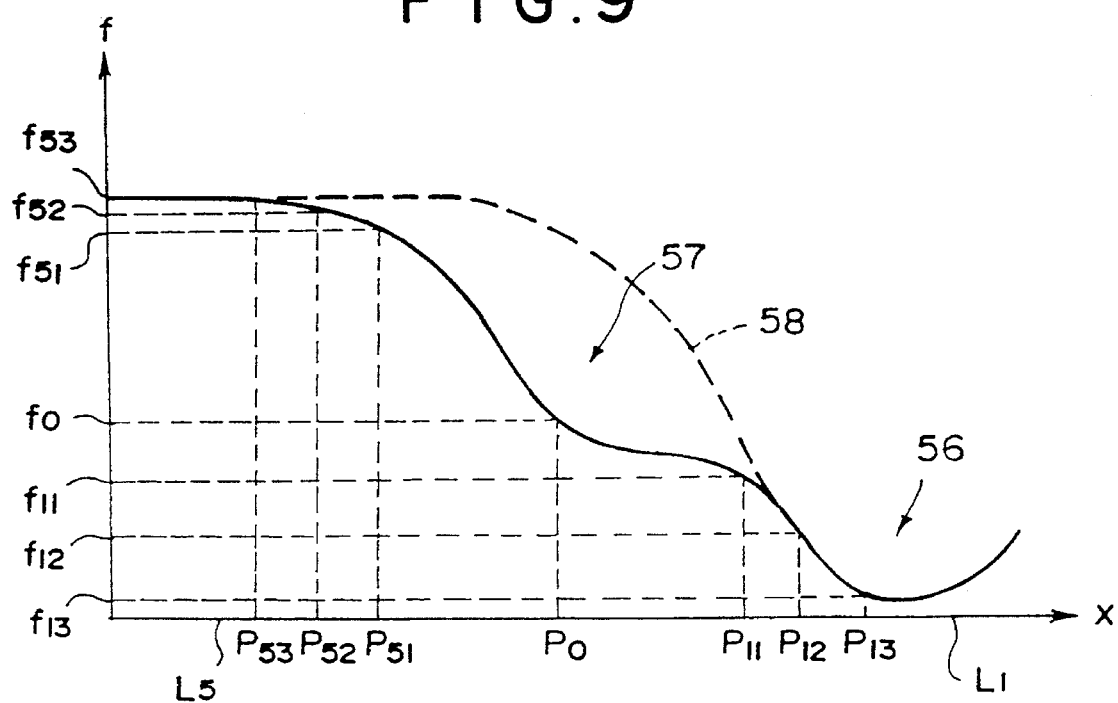
FIG. 9 is a graph showing an example of the profile of an X-ray image around a predetermined picture element P0 in the direction (x direction) along which the lines L1 and L5 shown in FIG. 8 extend.

FIG. 9 is a graph showing an example of the profile of the original image around a predetermined picture element P0 in the direction (x direction) along which the lines L1 and L5 shown in FIG. 8 extend. In this example, the predetermined picture element P0 is located approximately at the middle of a tumor pattern 57, which is close to a rib pattern 56. Typically, the profile of a tumor pattern (i.e. the distribution of the values of the image signal components representing the tumor pattern) is approximately symmetric bilaterally. However, in cases where, for example, the tumor pattern 57 is close to a rib pattern 56 as in the illustrated example, it often occurs that the profile of the tumor pattern 57 is not symmetric bilaterally. It is important that the tumor pattern 57 can be detected even in such cases. In FIG. 9, the broken line 58 represents an example of the profile of the original image including no tumor pattern.

As shown in FIG. 8, a plurality of (in this case, eight) imaginary lines $L_i$, where $i=1, 2, \ldots, 8$, extend from the predetermined picture element P0 in the X-ray image to peripheral parts of the X-ray image. Also, imaginary circles $R_j$, where $j=1, 2, 3$, having radii $r_1$, $r_2$, and $r_3$ extend around the predetermined picture element P0. The image signal component $f_0$ representing the predetermined picture element P0 is found. Also, the image signal components $f_{ij}$, where $i=1, 2, \ldots, 8$ and $j=1, 2, 3$, are found which represent the picture elements $P_{ij}$ located at the intersections of each of the lines $L_i$ and the circles $R_j$. (In FIG. 8, P11, P12, and P13 denote picture elements located at the intersections of a line L1 and circles R1, R2, and R3. Also, P51, P52, and P53 denote the picture elements located at the intersections of a line L5 and the circles R1, R2, and R3.)

Thereafter, differences $\Delta_{ij}$ between the value of the image signal component $f_0$ representing the predetermined picture element P0 and the values of the image signal components $f_{ij}$ representing the picture elements $P_{ij}$ are calculated from Formula (11), which is expressed as $$\Delta_{ij} = f_{ij} - f_0 \tag{11}$$

$(i=1, 2, \ldots, 8; j=1, 2, 3)$

For each of the lines $L_i$, the maximum value of the differences $\Delta_{ij}$, which have been calculated from Formula (11), is then found. Specifically, for the line L1, the maximum value of the differences between the value of the image signal component $f_0$ representing the predetermined picture element P0 and the values of the image signal components $f_{11}$, $f_{12}$, and $f_{13}$ representing the picture elements P11, P12, and P13 is found. The differences can be expressed as $$\Delta 11 = f11 - f0$$

$$\Delta 12 = f12 - f0$$

$$\Delta 13 = f13 - f0$$

In this example, as illustrated in FIG. 9, $\Delta 13 < \Delta 12 < \Delta 11 < 0$, and therefore the difference $\Delta 11$ is found to be the maximum value.

For the line L5, the maximum value of the differences between the value of the image signal component f0 representing the predetermined picture element P0 and the values of the image signal components f51, f52, and f53 representing the picture elements P51, P52, and P53 is also found. The differences are expressed as $$\Delta 51 = f51 - f0$$

$$\Delta 52 = f52 - f0$$

$$\Delta 53 = f53 - f0$$

In this example, the difference $\Delta 53$ is found to be the maximum value.

In the manner described above, for each of the lines Li, the differences between the value of the image signal component f0 representing the predetermined picture element P0 and the values of the image signal components fij representing the picture elements Pij are calculated, and the maximum value of the differences is found. Therefore, tumor patterns having various sizes can be detected.

Thereafter, calculations are made to find the mean-level value, for example, the mean value, of two maximum values, which have been found for each set of two lines extending from the predetermined picture element P0 in opposite directions. Specifically, mean values M15, M26, M37, and M48 are calculated respectively for the set of lines L1 and L5, the set of lines L2 and L6, the set of lines L3 and L7, and the set of lines L4 and L8. For the set of lines L1 and L5, the mean value M15 is given by the formula $$M15 = \frac{\Delta 11 + \Delta 53}{2} \quad (12)$$

As described above, two lines extending from the predetermined picture element P0 in opposite directions are grouped into a single set. Therefore, a tumor pattern can be detected accurately even when, as shown in FIG. 9, it is present in the vicinity of, for example, a rib pattern and the distribution of the values of the image signal components representing the tumor pattern is asymmetric.

From the mean values M15, M26, M37, and M48, which have been calculated in the manner described above, a characteristic value C1 is calculated in the manner described below. The characteristic value C1 is used during the judgment as to whether the predetermined picture element P0 falls or does not fall within the region corresponding to the tumor pattern.

Figure 10:
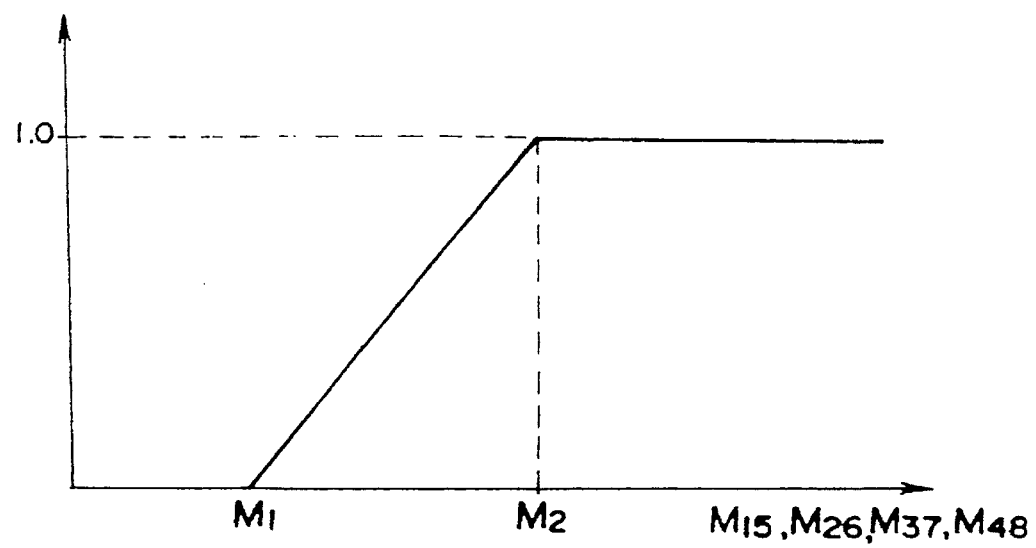
FIG. 10 is a graph showing how a characteristic value is determined which is used during a judgment as to whether a predetermined picture element P0 falls or does not fall within the region corresponding to a tumor pattern.

FIG. 10 is a graph showing how the characteristic value C1 is determined. In FIG. 10, the horizontal axis represents the mean values M15, M26, M37, and M48, which have been calculated in the manner described above. The vertical axis represents rating values C15, C26, C37, and C48, which correspond respectively to the mean values M15, M26, M37, and M48.

A rating value of zero is assigned to the mean values M15, M26, M37, and M48 in cases where they are smaller than a certain value M1. A rating value of 1.0 is assigned to the mean values M15, M26, M37, and M48 in cases where they are larger than a certain value M2. In cases where the mean values M15, M26, M37, and M48 fall within the range of M1 to M2, a rating value falling within the range of 0.0 to 1.0 is assigned to the mean values M15, M26, M37, and M48, depending upon their values. In this manner, the rating values C15, C26, C37, and C48 are found, which correspond respectively to the mean values M15, M26, M37, and M48. The sum of the rating values C15, C26, C37, and C48, which is expressed as $$C1 = C15 + C26 + C37 + C48 \quad (13)$$

is taken as the characteristic value C1. The characteristic value C1 will fall within the range of a minimum value 0.0 to a maximum value 4.0.

The characteristic value C1 is then compared with a predetermined threshold value Th2. From whether $C1 \geq Th2$ or $C1 < Th2$, the judgment is made as to whether the predetermined picture element P0 falls or does not fall within the region corresponding to the tumor pattern.

In the original image, the rib patterns are present in the lung field regions 16a and 16b. Therefore, in the manner described below, when the image signal components corresponding to the soft tissues in the lung field regions 16a and 16b in the original image are processed with the aforesaid filter, the filter is modified adaptively for the image signal components corresponding to the region in the vicinity of the rib patterns.

Figure 11:
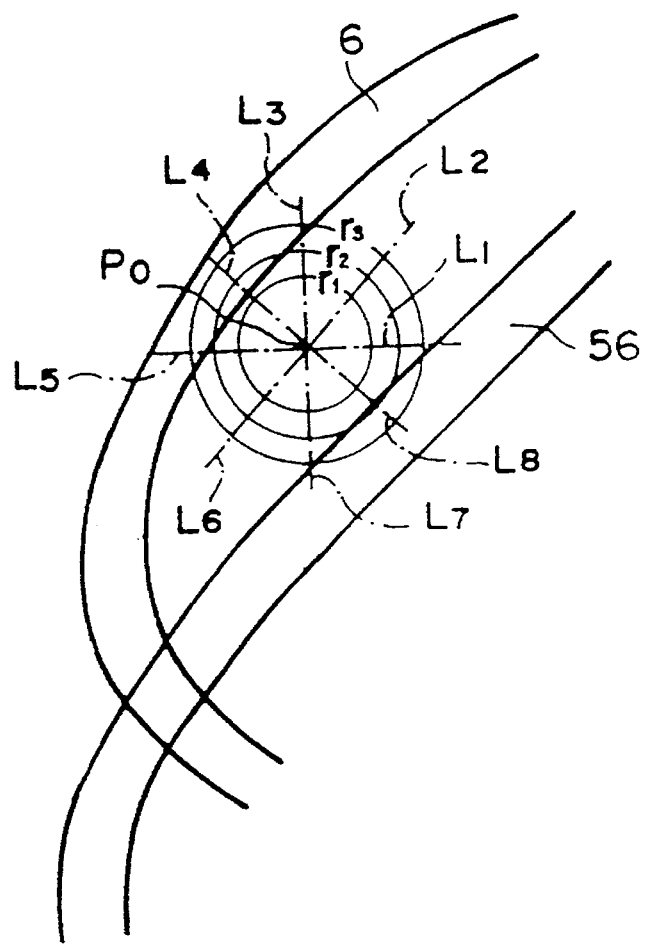
FIG. 11 is an enlarged view showing part of rib patterns (not shown in FIG. 6) in the lung field regions 16a and 16b shown in FIG. 6.

FIG. 11 is an enlarged view showing part of rib patterns (not shown in FIG. 6) in the lung field region 16a or the lung field region 16b shown in FIG. 6. In FIG. 11, the filter shown in FIG. 8 is also illustrated.

As illustrated in FIG. 11, part of the filter overlaps the rib patterns 56, 56. Therefore, when a characteristic value corresponding to a predetermined picture element P0 shown in FIG. 11 is calculated, the information about r1 and r2 is utilized for the lines L1, L3, L5, and L7. For the lines L2 and L6, the information about r1, r2 and r3 is utilized. Also, for the lines L4 and L8, only the information about r1 is utilized. In this manner, the spatial-domain filter is modified adaptively in accordance with the information about the positions of the rib patterns. Therefore, the calculation of the characteristic value C1 is not adversely affected by the rib patterns.

No limitation is imposed on the algorithms in the filter, which is employed to find the tumor patterns. Another example of the filter will be described hereinbelow. The filter described below is proposed in U.S. patent application Ser. No. 542,487.

Specifically, calculations are made to find the gradients $\nabla fij$ of the image signal components fij representing the picture elements Pij, where $i=1, 2, \ldots, 8$ and $j=1, 2, 3$, which are shown in FIG. 8.

The term "gradient" as used herein means the vector expressed as $$\nabla f(m,n) = (f(m+1,n) - f(m,n), f(m,n+1) - f(m,n)) \quad (14)$$

In Formula (14), (m,n) denotes the x and y coordinates of a certain picture element P in a radiation image, (m+1,n) denotes the coordinates of a picture element P', which is adjacent to the picture element P in the x direction, and (m,n+1) denotes the coordinates of a picture element P", which is adjacent to the picture element P in the y direction. Also, f(m,n), f(m+1,n), and f(m,n+1) respectively denote the values of the image signal components representing the picture elements P, P', and P".

Figure 12:
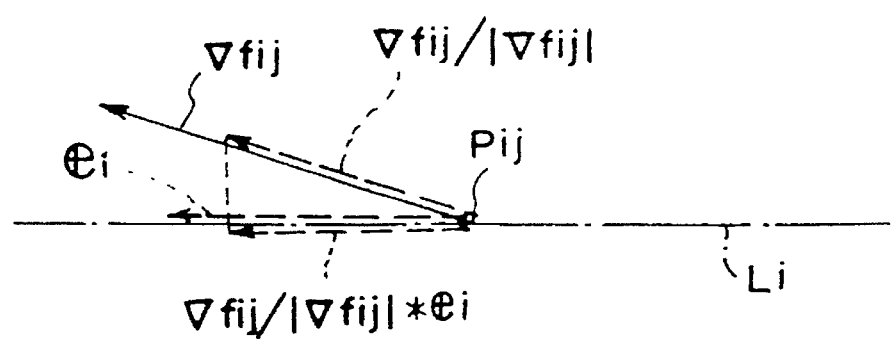
FIG. 12 is an explanatory view showing the vector of a gradient $\nabla fij$ of an image signal component fij.

FIG. 12 shows the gradient of an image signal component fij. How it is calculated is described below.

After the gradients $\nabla fij$ have been calculated, the magnitudes of the gradients $\nabla fij$ are made equal to 1.0. Specifically, the normalized gradients $\nabla fij/|\nabla fij|$ can be calculated by dividing the gradients $\nabla fij$ by their magnitudes $|\nabla fij|$.

Thereafter, the projections of the normalized gradients $\nabla fij/|fij|$ onto the vectors directed from the picture elements Pij to the predetermined picture element P0 are calculated. The projections are expressed as $\nabla fij/|\nabla fij|* e_i$, where $e_i$ denotes the unit vectors directed from the picture elements Pij to the predetermined picture element P0, and * denotes the inner product.

As for the sign of the projections, the direction heading towards the predetermined picture element P0 is taken as positive, and the direction heading away from the predetermined picture element P0 is taken as negative. For each of the lines Li, where i=1, 2, ..., 8, the maximum value of the projections is found. The maximum value is expressed as $$\{\nabla fij/|\nabla fij| * e_i\}_M$$

(i=1,2, ... ,8)

Thereafter, the sum of the maximum values which were found for each of the respective lines Li is calculated. This sum is expressed as $$\sum_{i=1}^{8} \{\nabla fij/|\nabla fij| * e_i\}_M$$

The sum expressed as $$\sum_{i=1}^{8} \{\nabla fij/|\nabla fij| * e_i\}_M$$

is taken as a characteristic value C2. The characteristic value C2 is then compared with a predetermined threshold value Th3. From whether $C2 \geq Th3$ or $C2 < Th3$, a judgment is made as to whether the predetermined picture element P0 falls or does not fall within the region corresponding to the tumor pattern.

With the filter described above, the gradients $\nabla fij$ are normalized, and only the projections thereof (i.e. the extent of differences in the value of the signal components in the directions of the lines Li) onto vectors directed from the picture elements Pij to the predetermined picture element P0 are taken into consideration. Therefore, a characteristic value C2 is obtained, which will be large for a tumor pattern having a circular shape and which does not depend on the contrast of the tumor pattern with respect to the image regions around the tumor pattern. Accordingly, the tumor pattern can be detected accurately.

A further example of the filter utilizing different algorithms will be described hereinbelow. The filter described below is proposed in U.S. patent application Ser. No. 542,487.

As shown in FIG. 8, the area of a center region Q0 including the predetermined picture element P0 is selected. Also, the areas of peripheral regions Qij, where i=1, 2, ..., 8 and j=1, 2, 3, are selected for each of the lines Li. Each of the peripheral regions Qij includes one of a plurality of picture elements Pij, where i=1, 2, ..., 8 and j=1, 2, 3. (In FIG. 8, Q11, Q12, Q13, Q51, Q52, and Q53 denote the peripheral regions which respectively include the picture elements P11, P12, P13, P51, P52, and P53.)

Thereafter, a calculation is made to find a mean-level value Q0 of the values of image signal components representing a plurality of picture elements, which are located in the center region Q0. Also, calculations are made to find mean-level values Qij, where i=1, 2, ..., 8 and j=1, 2, 3, each representing the mean level of the values of image signal components representing a plurality of picture elements located in each of the peripheral regions Qij, where i=1, 2, ..., 8 and j=1, 2, 3. As an aid in facilitating the explanation, Q0 represents both the center region and the mean-level value of the values of image signal components representing the picture elements, which are located in the center region. Also, Qij, where i=1, 2, ..., 8 and j=1, 2, 3, represents both the peripheral regions and the mean-level values representing the mean level of the values of the image signal components representing the picture elements, which are located in each of the peripheral regions.

Thereafter, differences $\Delta ij$, where i=1, 2, ..., 8 and j=1, 2, 3, between the mean-level value Q0 corresponding to the center region and the respective mean-level values Qij corresponding to the peripheral regions are calculated from the formula $$\Delta ij = Qij - Q0 \qquad (15)$$

For each of the lines Li, the maximum value $\Delta i$ of the differences $\Delta ij$ is then found. Specifically, as for the line L1, a maximum value $\Delta 1$ is found from $\Delta 11$, $\Delta 12$, and $\Delta 13$. As for the line L5, a maximum value $\Delta 5$ is found from $\Delta 51$, $\Delta 52$, and $\Delta 53$.

A first characteristic value U is then found, which is representative of the maximum values $\Delta i$, where i=1, 2, ..., 8, which have been found for the plurality of the lines Li. Also, a second characteristic value V is found, which represents the amount of dispersion in the maximum values $\Delta i$, where i=1, 2, ..., 8. For this purpose, first, characteristic values U1, U2, U3, and U4, and characteristic values V1, V2, V3, and V4 are calculated from the formulas $$U1 = (\Delta 1 + \Delta 2 + \Delta 5 + \Delta 6)/4 \qquad (16)$$

$$U2 = (\Delta 2 + \Delta 3 + \Delta 6 + \Delta 7)/4 \qquad (17)$$

$$U3 = (\Delta 3 + \Delta 4 + \Delta 7 + \Delta 8)/4 \qquad (18)$$

$$U4 = (\Delta 4 + \Delta 5 + \Delta 8 + \Delta 1)/4 \qquad (19)$$

$$V1 = U1/U3 \qquad (20)$$

$$V2 = U2/U4 \qquad (21)$$

$$V3 = U3/U1 \qquad (22)$$

$$V4 = U4/U2 \qquad (23)$$

By way of example, the process for calculating the characteristic value U1 from Formula (16) has the effects described below. Specifically, the addition of the maximum values corresponding to two adjacent groups of peripheral regions, which are located on the same side with respect to the predetermined picture element P0, (i.e. the addition of $\Delta 1$ and $\Delta 2$, or the addition of $\Delta 5$ and $\Delta 6$) corresponds to a smoothing process. Also, the maximum values corresponding to peripheral regions, which are located on opposite sides with respect to the predetermined picture element P0, are added together (in the case of Formula (16), the sum of $\Delta 1$ and $\Delta 2$ and the sum of $\Delta 5$ and $\Delta 6$ are added together). Such an addition is carried out in order that a tumor pattern can be detected even when, as shown in FIG. 9, the distribution of the values of the image signal components representing the tumor pattern is asymmetric.

As for the calculation of the characteristic value V1 from Formula (20), the characteristic values U1 and U3 represent characteristics of the image in directions which are perpendicular to each other. Therefore, in cases where the shape of the tumor pattern is circular in FIG. 9, V1 will be approximately equal to 1.0. In cases where the predetermined picture element P0 is present in a linear pattern, such as a rib pattern, V1 will not be equal to 1.0.

As the first characteristic value U, which is representative of the maximum values Δi, where i=1, 2, 8, of the aforesaid differences, the maximum value of the characteristic values U1, U2, U3, and U4, i.e.

$$U = MAX(U1, U2, U3, U4) \quad (24)$$

is employed. Also, as the second characteristic value V, which represents the amount of dispersion in the maximum values Δi, where i=1, 2, ..., 8, of the aforesaid differences, the maximum value of the characteristic values V1, V2, V3, and V4, i.e.

$$V = MAX(V1, V2, V3, V4) \quad (25)$$

is employed. After the first characteristic value U and the second characteristic value V have been found in the manner described above, a characteristic value C3 is calculated and then used during the judgment as to whether a predetermined picture element P0 falls or does not fall within the region corresponding to the tumor pattern. As the characteristic value C3, the ratio of the first characteristic value U to the second characteristic value V is employed, which is expressed as $$C3 = U/V \quad (26)$$

The characteristic value C3 is then compared with a predetermined threshold value Th4. From whether C3≧Th4 or C3<Th4, the judgment is made as to whether the predetermined picture element P0 falls or does not fall within the region corresponding to the tumor pattern.

In the examples of the filters described above, eight imaginary lines, L1 through L8, are drawn around a predetermined picture element P0 in an X-ray image. However, the number of lines Li is not limited to eight, but may, for example, be 16. Also, the distances from the predetermined picture element P0 are not limited to the three distances (r1, r2, and r3). For example, in cases where the sizes of the tumor patterns, which are to be detected, are approximately the same, only a single distance need be employed. Also, in order for tumor patterns having various sizes to be detected more accurately, operations may be carried out for a plurality of distances whose lengths vary approximately continuously between the length of the distance r1 and the length of the distance r3.

Also, the abnormal pattern finding means 3 may employ any of other filters. Additionally, different filters may be employed for the original image and the soft tissue image. Moreover, different filters may be employed for different regions in the original image or the soft tissue image.

In the aforesaid embodiment of the abnormal pattern detecting apparatus in accordance with the present invention, from X-ray images of the chest of a human body, which images have been stored on stimulable phosphor sheets, tumor patterns are detected which appear, typically, as circular patterns on the X-ray images. However, the abnormal pattern detecting apparatus in accordance with the present invention is not limited to the detection of circular tumor patterns nor to the processing of X-ray images of chests. Also, recording media other than stimulable phosphor sheets may be used. The abnormal pattern detecting apparatus in accordance with the present invention is applicable widely when, from image signals representing radiation images of an object, abnormal patterns in the radiation images are detected.

I claim:

1. Apparatus for detecting an abnormal pattern from a plurality of image signals representing a radiation image of an object which is constituted of soft tissues and bones, comprising:

an image operating circuit for generating from the plurality of image signals at least:
   a) an original image signal corresponding to an original image representing the soft tissues and the bones of said object, and
   b) a soft tissue image signal corresponding to a soft tissue image primarily representing soft tissues of said object, wherein said original image signal and said soft tissue image signal are generated from the plurality of image signals representing a radiation image which has been recorded by exposing said object to at least two kinds of radiation having different energy distributions, wherein the different energy distributions exhibit different transmittances with respect to soft tissues and bones;

a region discriminating circuit which discriminates anatomical regions in the radiation image from at least one of said original image and soft tissue image signals, and provides an output indicative of different anatomical regions of said object; and an abnormal pattern finding circuit including an abnormal pattern finding filter, responsive to said original image and soft tissue image signals and to the output of said region discriminating circuit, said abnormal pattern finding circuit uniquely processing at least one of said original image signal and said soft tissue image signal and detecting an abnormal pattern, wherein, based on the output of said region discriminating circuit, said abnormal pattern finding circuit adaptively processes said original image signal to detect an abnormal pattern in the different anatomical regions of said object which include primarily soft tissues and processes said soft tissue image signal to detect an abnormal pattern in the different anatomical regions of said object which include primarily bones.

2. An apparatus as defined in claim 1 wherein said image operating circuit also generates a bone image signal corresponding to a bone image primarily representing the bones of said object, and wherein said region discriminating circuit finds the positions of bone patterns from said bone image signal.

3. An apparatus as defined in claim 2 wherein said abnormal pattern finding circuit processes one of said original image signal and said soft tissue image signal with an abnormal pattern finding filter in accordance with said anatomical regions and the positions of the bone patterns.

4. An apparatus as defined in claim 1 wherein said image operating circuit carries out superposition processing on the plurality of said image signals representing the plurality of said radiation images of said object and utilizes an image signal, which is obtained from the superposition processing, as said original image signal.

5. An apparatus as defined in claim 4 wherein said region discriminating circuit discriminates anatomical regions in the radiation image from said original image signal, which has been obtained from the superposition processing.

6. An apparatus as defined in claim 1 wherein said abnormal pattern finding filter is a spatial-domain filter.

7. An apparatus as defined in claim 1 wherein each of said radiation images of said object has been stored on a stimulable phosphor sheet.

8. An apparatus as defined in claim 7 wherein the image signals of said radiation images are obtained from a read-out operation wherein said stimulable phosphor sheet is exposed to stimulating rays, which cause said stimulable phosphor sheet to emit light in proportion to the amount of energy stored thereon during its exposure to radiation, and the emitted light is detected photoelectrically.

9. An apparatus as defined in claim 8 wherein said stimulating rays are a laser beam.

10. An apparatus as defined in claim 1 wherein each of said radiation images of said object has been recorded on photographic film.

* * * * *